United States Patent
Gjoni et al.

(10) Patent No.: US 10,933,019 B2
(45) Date of Patent: Mar. 2, 2021

(54) LIQUID FORMULATIONS OF DAPTOMYCIN

(71) Applicant: XELLIA PHARMACEUTICALS APS, Copenhagen (DK)

(72) Inventors: Tina Gjoni, Zagreb (HR); Dubravka Strazic, Zagreb (HR)

(73) Assignee: XELLIA PHARMACEUTICALS APS, Copenhagen (DK)

( * ) Notice: Subject to any disclaimer, the term of this patent is extended or adjusted under 35 U.S.C. 154(b) by 0 days.

(21) Appl. No.: 16/343,443

(22) PCT Filed: Oct. 17, 2017

(86) PCT No.: PCT/EP2017/076519
§ 371 (c)(1),
(2) Date: Apr. 19, 2019

(87) PCT Pub. No.: WO2018/073269
PCT Pub. Date: Apr. 26, 2018

(65) Prior Publication Data
US 2019/0240155 A1  Aug. 8, 2019

Related U.S. Application Data

(60) Provisional application No. 62/411,024, filed on Oct. 21, 2016.

(51) Int. Cl.
| | |
|---|---|
| *A61K 9/08* | (2006.01) |
| *A61K 38/12* | (2006.01) |
| *A61K 47/18* | (2017.01) |
| *A61K 47/10* | (2017.01) |
| *A61K 47/26* | (2006.01) |
| *A61K 47/20* | (2006.01) |
| *A61K 47/14* | (2017.01) |
| *A61K 47/44* | (2017.01) |
| *A61P 31/04* | (2006.01) |

(52) U.S. Cl.
CPC .......... *A61K 9/08* (2013.01); *A61K 38/12* (2013.01); *A61K 47/10* (2013.01); *A61K 47/18* (2013.01); *A61K 47/20* (2013.01); *A61K 47/26* (2013.01); *A61P 31/04* (2018.01); *A61K 47/14* (2013.01); *A61K 47/44* (2013.01)

(58) Field of Classification Search
None
See application file for complete search history.

(56) References Cited

U.S. PATENT DOCUMENTS

| | | | | |
|---|---|---|---|---|
| 2006/0269485 A1* | 11/2006 | Friedman | ............... | A61K 9/107 424/45 |
| 2009/0186830 A1* | 7/2009 | Fujimoto | ............. | C07D 513/22 514/2.9 |
| 2013/0172271 A1* | 7/2013 | Fragale | .................. | A61K 38/12 514/21.1 |
| 2014/0323457 A1* | 10/2014 | Bottcher | ............... | A61K 31/047 514/183 |
| 2015/0216928 A1* | 8/2015 | Chetlapalli | ............ | A61K 38/15 514/2.9 |
| 2016/0346294 A1* | 12/2016 | Sengupta | ............... | A61K 47/36 |
| 2017/0348382 A1* | 12/2017 | Kurade | .................. | A61K 38/12 |
| 2018/0327367 A1* | 11/2018 | Chen | .................... | C07K 5/1024 |
| 2019/0153010 A1* | 5/2019 | Miller | .................... | A61K 31/43 |

FOREIGN PATENT DOCUMENTS

| | | |
|---|---|---|
| CN | 103006562 A | 4/2013 |
| EP | 0386951 | 9/1990 |
| WO | 2011035108 A1 | 3/2011 |
| WO | 2011062676 | 5/2011 |
| WO | 2011062676 A1 | 5/2011 |
| WO | 2011063419 A2 | 5/2011 |
| WO | 2013103801 A1 | 7/2013 |
| WO | 2014041425 A1 | 3/2014 |
| WO | 2014045296 A2 | 3/2014 |
| WO | 2016059587 A1 | 4/2016 |
| WO | 2016059592 A1 | 4/2016 |
| WO | 2016098009 A1 | 6/2016 |

OTHER PUBLICATIONS

Brennan et a;., "Spontaneous Degradation of Polypeptides at Aspartyl and Asparaginyl Residues: Effects of the Solvent Dielectric"; Protein Science; 2; pp. 331-338; (1993).

Kirsch et al.; "Kinetics of the Aspartyl Transpeptidation of Daptomycin, a Novel Lipopeptide Antibiotic"; Pharmaceutical Research; 6(5); pp. 387-393; (1989).

Mottu et al.; "Organic Solvents for Pharmaceutical Parenterals and Embolic Liquids: A Review of Toxicity Data"; PDA J Pharm Sci and Tech; 54; pp. 456-469; (2000).

Muangsiri et al.; "Studies on the Reactions Between Daptomycin and Glyceraldehyde"; International Journal of Pharmaceutics; 289; pp. 133-150; (2005).

Muangsiri et al.; "The Kinetics of the Alkaline Degradation of Daptomycin"; Journal of Pharmaceutical Sciences; 90 (8); pp. 1066-1075; (2001).

Wakankar et al.; "Formulation Considerations for Proteins Susceptible to Asparagine Deamidation and Asparate Isomerization"; Journal of Pharrnaceucital Sciences; 95(11); pp. 2321-2336; (2006).

International Search Report and Written Opinion; International Application No. PCT/EP2017/076519; International filing Date Oct. 17, 2017; dated Jan. 10, 2018; 14 pages.

\* cited by examiner (Continued)

*Primary Examiner* — Sin J Lee
(74) *Attorney, Agent, or Firm* — Cantor Colburn LLP

(57) ABSTRACT

The present invention relates to liquid pharmaceutical compositions comprising daptomycin, methods of providing such compositions and the use thereof. Provided herein are formulations comprising daptomycin, one or more polar protic solvents, and mixtures thereof. Formulations according to the present invention can further comprise polar aprotic solvent and/or source of calcium.

21 Claims, No Drawings

LIQUID FORMULATIONS OF DAPTOMYCIN

CROSS REFERENCE TO RELATED APPLICATIONS

This application is a National Stage application of PCT/EP2017/076519, filed on Oct. 17, 2017, which claims the benefit of U.S. Provisional Application No. 62/411,024, filed on Oct. 21, 2016, both of which are incorporated by reference in their entirety herein.

FIELD OF THE INVENTION

The present invention relates to liquid pharmaceutical compositions comprising daptomycin, methods of providing such compositions and the use thereof.

BACKGROUND OF THE INVENTION

Lipopeptides represent a class of powerful anti-infective drugs which exhibit highly effective antibacterial action against multi-resistant bacteria, as well as antifungal activity. A wide variety of lipopeptide drugs, such as daptomycin, are now available on the market in order to fight invasive and often life-threatening infections.

Daptomycin is the first cyclic lipopeptide antibiotic approved by the U.S. Food and Drug Administration (FDA) in 2003, for the treatment of infections caused by Gram-positive pathogens, including methicillin- and vancomycin-resistant strains. Due to unique mechanism of action distinct from all other antimicrobial agents available in the market, daptomycin is able to overcome the mechanisms of resistance that many resistant strains have developed, and considering that rare incidences of clinical resistance to daptomycin are reported, the drug has become very important for current clinical practice.

Daptomycin (Structure 1) is composed of a decanoyl side chain attached to the N-terminus of a 13-amino acid peptide, wherein ten of the amino acids form a cyclic structure and the other three form a chain.

The cyclic section of the molecule is linked to the side chain through an ester bond between the C-terminal carboxyl group of kynurenine and the fourth residue (threonine).

Structure 1

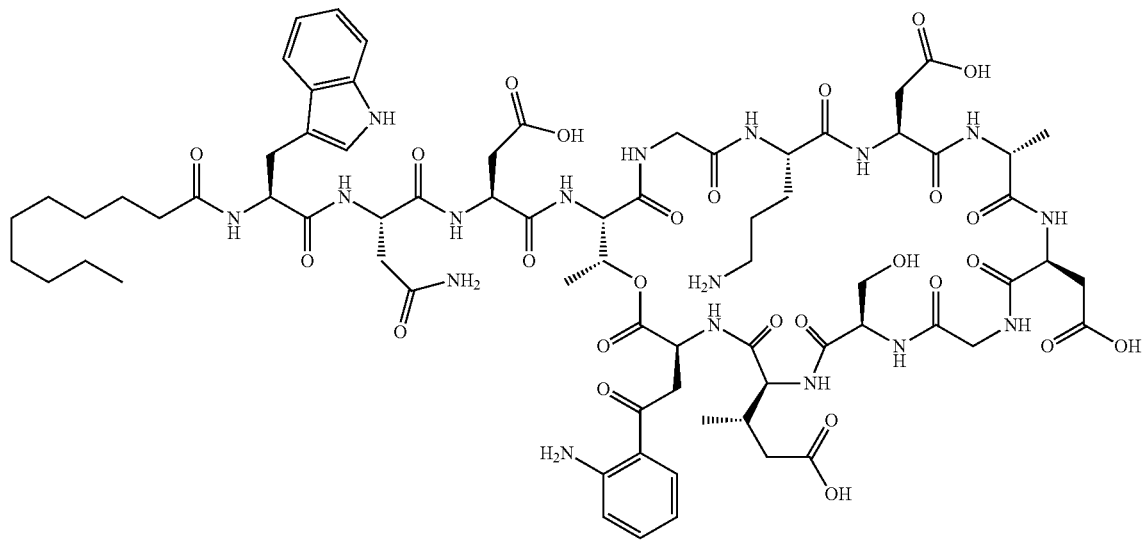

Molecular structure of daptomycin

According to the available literature, it is extremely difficult to stabilize daptomycin in solutions due to the fact that daptomycin is susceptible to hydrolytic degradation and is known to degrade by aspartyl transpeptidation at asp-9 residue in mildly acidic solutions.

According to Kirsch et al. *Pharmaceutical Research*, 1989, Muangsiri et al., *International Journal of Pharmaceutics*, 2005, and Muangsiri et al., *Journal of Pharmaceutical Sciences*, 2001, this degradation pathway involves the formation of a succinimido intermediate (anhydrodaptomycin) formed by attack of carbonyl carbon of Asp9 side chain and subsequent reversible formation of two aspartic acid isomers formed by rehydration of the anhydrodaptomycin succinimide.

Kirsch et al. *Pharmaceutical Research*, 1989, and Muangsiri et al., *Journal of Pharmaceutical Sciences*, 2001, page 1067, additionally disclose that unknown, parallel pathways of daptomycin loss have been observed and are thought to include asparaginyl deamidation, ester hydrolysis, and/or peptide bond cleavage.

The degradation pathways of daptomycin under acidic, neutral, and alkaline conditions are known as ester hydrolysis occurring in alkaline condition, aspartyl transpeptidation as the predominant pathway in the pH range of 3-6 and unknown degradation pathway which occurs at low pH. Besides dependency of impurity formation on pH, they are also temperature dependent.

In light of its instability in solution, daptomycin is currently commercially available only in a form of lyophilized powder for intravenous infusion (Cubicin® and Cubicin RF®) which requires reconstitution and subsequent dilution step prior to patient administration.

Considering that daptomycin is administered intravenously on a daily basis during long-term treatment, and often only the reconstitution step takes of about 30 minutes or even more, lyophilized powder is not a convenient and practical form for medical professionals to handle.

Limited stability of reconstituted and diluted formulations is also an obvious drawback of such a valuable drug.

Accordingly, formulations of daptomycin that do not require lyophilization and/or reconstitution and exhibit typical storage physico-chemical stability are needed.

The disclosure provided in WO2011063419 discloses powder daptomycin formulations with improved chemical stability and faster reconstitution times when in the solid state. However, liquid compositions without the need for lyophilization and being stable for prolonged time are not disclosed.

WO2014041425 also discloses lyophilized daptomycin formulations having improved reconstitution times. Again, no stable liquid compositions are disclosed without the need for lyophilization.

Invention described in WO2014045296 relates to stable pharmaceutical formulation comprising daptomycin. However, lyophilization is needed.

WO2013103801 reports powdered formulations comprising daptomycin and polyethylene glycol.

WO2016098009 relates to lyophilized compositions comprising daptomycin.

Kirsch et al. (*Pharmaceutical Research*, 1989) describe aqueous solutions of daptomycin with the pH range of 3 to 8, wherein daptomycin degradation products (anhydrodaptomycin and beta isomer) formations are investigated through different pH conditions. However, they were unable to stabilize daptomycin in solution and to prevent degradation formation.

Liquid compositions of daptomycin have been reported in WO2011062676 and WO2011035108, filed by the same applicant, however those compositions comprise daptomycin in considerably lower concentrations of up to 25 mg/mL.

Invention disclosed in EP0386951 provides formulations of daptomycin and different buffers, which allow daptomycin to be prepared in 5% dextrose.

WO2016059587 and WO2016059592 relate to stable, non-aqueous and ready-to-use injectable composition of daptomycin. However, according to the description, water content of such formulations is less than 2%, since it is well known that daptomycin degrades at fast rate in aqueous solutions.

SUMMARY OF THE INVENTION

The present invention was made in view of the prior art and current medical practitioners needs, and is dealing with the problem of providing stable daptomycin liquid pharmaceutical formulations as a contrast to inconvenient and potentially problematic methods of lyophilized drug preparation and administration, wherein the liquid formulations of daptomycin offer the advantage of easiness of handling with a high degree of patient acceptability and compliance.

Provided herein are stable liquid pharmaceutical formulations comprising daptomycin and one or more solvents selected from the group consisting of polar protic solvents, and mixtures thereof.

In accordance of the present invention, provided are stable liquid pharmaceutical formulations comprising daptomycin, one or more solvents selected from the group consisting of polar protic solvents and further comprising a polar aprotic solvent, and mixtures thereof.

Encompassed by the present invention are formulations as disclosed above, further comprising calcium.

Additionally, compositions of the present invention may further comprise one or more pharmaceutically acceptable excipients such as carriers, antioxidants, surfactants, lipids, sugars, organic acids, complexing agents, preservatives, stabilizers, bulking agents, surfactants, buffers, carriers, diluents, vehicles, solubilizers and binders.

According to the present invention, concentration of daptomycin in solutions may range from about 10 mg/mL to about 120 mg/mL.

Surprisingly it was found when daptomycin is formulated in solutions according to the present invention, degradation products formation is retarded, and accordingly, such solutions are stable both chemically and physically and provide more flexible storage conditions and handling.

As a further advantage of the present invention, water content of the disclosed compositions may be up to about 15% w/V.

Formulations provided herein can be stored at room temperature (25° C.), below room temperature, such as temperature of about 20° C., about 15° C., about 10° C., and refrigerated conditions such as 2-8° C.

Methods of making and using formulations of daptomycin for treatment of microbial infections, particularly caused by Gram-positive organisms, are also described.

Other objects, features and advantages of the present invention will become apparent from the following detailed description and examples. It should be understood, however, that the detailed description and the examples, while indicating specific embodiments of the invention, are given by way of illustration only, and are not intended to limit the breadth or scope of the invention concepts in any manner.

DETAILED DESCRIPTION OF THE INVENTION

Stable and pharmaceutically acceptable liquid compositions of daptomycin have been discovered and reported herein.

Term "stable" as used herein, refers to a pharmaceutical formulation containing daptomycin having sufficient stability to have utility as a pharmaceutical product.

The disclosed formulations exhibit acceptable stability with regard to retaining the daptomycin efficacy and potency in solution dosage form, avoid unacceptable degradation of active substance to undesired related substances, and retain pharmaceutically desirable appearance such as acceptable color, clarity and no visible particles.

By terms "pharmaceutical composition" or "pharmaceutically acceptable composition" as used herein, is meant a composition that it is suitable for veterinary use as well as human pharmaceutical use, wherein such composition is generally safe, relatively non-toxic and does not cause unacceptable side effects, and contains pharmaceutically acceptable excipients, e.g. without limitation to solvents, carriers, antioxidants, surfactants, lipids, sugars, organic acids, complexing agents, preservatives, stabilizers, bulking agents, surfactants, buffers, carriers, diluents, vehicles, solubilizers and binders.

As used herein, the terms "pharmaceutical composition", "pharmaceutical formulation", "composition" and "formulation" are used interchangeably.

In view of excipients, without limitation to solvents, carriers, antioxidants, surfactants, lipids, sugars, organic acids, complexing agents, preservatives, stabilizers, bulking agents, surfactants, buffers, carriers, diluents, vehicles, solubilizers and binders etc., as used herein, "pharmaceutically acceptable" is meant that they are useful in preparing a pharmaceutical composition that is generally non-toxic and neither biologically nor otherwise undesirable, further that they do not cause unacceptable loss of pharmacological activity of the drug in question, and are acceptable for use in treatment of humans and/or animals.

The language "therapeutically effective amount" of the daptomycin compound, as used herein, refers to an amount of daptomycin administered to a patient sufficient to produce a therapeutic response to one or more of the symptoms of the disease being treated.

As used herein, the term "about" is defined as ±10% of the numerical value or range in question.

Daptomycin degrades upon exposure to liquid(s), especially water, to three main degradation products.

First degradation product is identified as anhydrodaptomycin (Structure 2.), which forms by aspartyl transpeptidation at asp-9 residue.

Structure 2

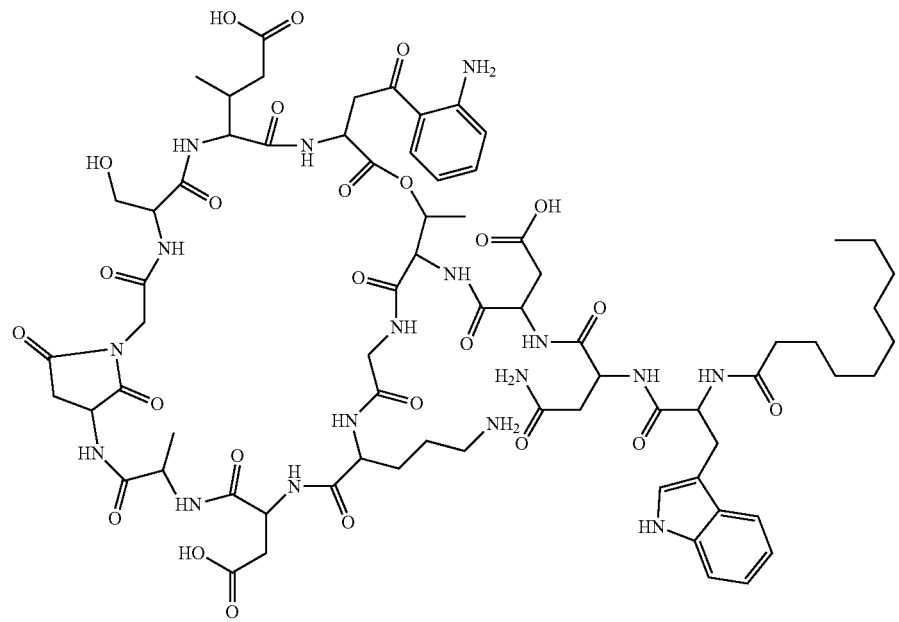

Anhydroaptomycin impurity

Second undesirable product of daptomycin degradation is beta (ß-aspartyl) isomer (Structure 3) formed with the rehydration of anhydrodaptomycin.
Structure 3
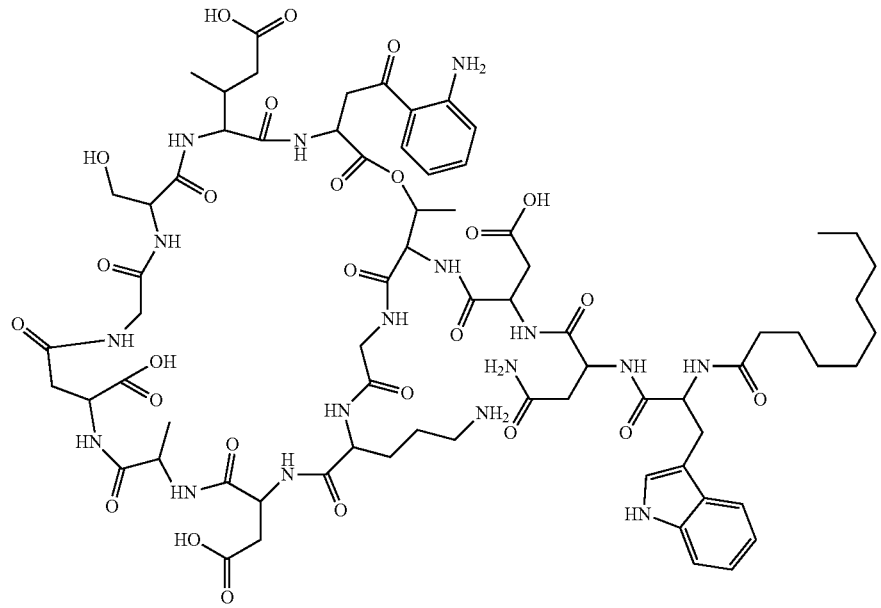
Beta (β-aspartyl) isomer impurity
Another undesirable compound that daptomycin degrades to is lactone hydrolysis product (Structure 4).
Structure 4
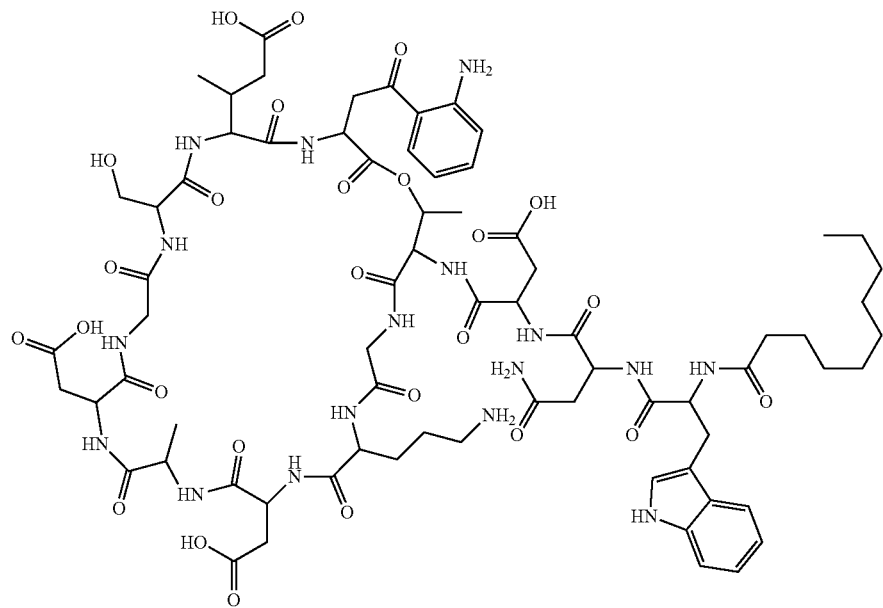
Lactone hydrolysis product impurity As used herein, "stable" is defined either as no more than about 10% of total impurities formation, determined by HPLC analysis, or as no more than about 5% of every individual impurity formation, determined by HPLC analysis, under typical storage conditions.

Analysis of the liquid formulations of the present invention can be performed using techniques known in the art, including HPLC, gas chromatography, and NMR.

In preferred embodiments, formulations are stable in view of no more than about 10% of total impurities formation with the second limitation wherein no individual impurity is more than about 5%, determined by HPLC analysis, under typical storage conditions.

For example, compositions according to this invention are stable if anhydrodaptomycin impurity is about 5% or lower, beta about 5% or lower and lactone hydrolysis product is about 5% or lower and if total impurities are no more than about 10%.

Stable pharmaceutical compositions of daptomycin, according to the present invention, have sufficient stability to allow typical storage at a convenient temperature, wherein the typical storage temperature range is from 2° C. to 30° C., for a reasonable period of time.

According to the present invention, disclosed pharmaceutically acceptable formulations of daptomycin are stable over the course of typical storage conditions, including time periods of about 7 days (1 week), about 14 days (2 weeks), about 30 days (1 month), about 60 days (2 months), about 150 days (5 months), about 180 days (6 months), about 12 months (1 year) and longer at temperatures of about 25° C. (room temperature), below room temperatures, and refrigerated temperatures, for example, about 2-8° C.

Preferably, the liquid formulations of the present invention are stored at refrigerated temperatures, e.g. 2-8° C.

In preferred embodiments, formulations of the present invention will exhibit 5.0% or less of anhydrodaptomycin, determined by HPLC analysis, after about 7 days (1 week) or longer, stored at temperatures of about 2-8° C.

Additionally, formulations of the present invention will exhibit 5.0% or less of anhydrodaptomycin, determined by HPLC analysis, after being stored about 7 days (1 week) or longer at temperature about 25° C.

In other embodiments of the present invention, formulations described herein will exhibit about 5.0% or less of beta isomer, as determined by HPLC analysis, after about 7 days (1 week) or longer, stored at temperatures of about 2-8° C.

Additionally, formulations of the present invention will exhibit 5.0% or less of beta isomer, determined by HPLC analysis, after being stored about 7 days (1 week) or longer at temperature about 25° C.

In other embodiments of the present invention, formulations will exhibit about 5% or less of lactone hydrolysis product, as determined by HPLC analysis, after about 7 days (1 week) or longer, stored at temperatures of about 2-8° C.

In other embodiments of the present invention, formulations will exhibit about 5% or less of lactone hydrolysis product, as determined by HPLC analysis, after about 7 days (1 week) or longer, stored at temperatures of about 25° C.

In certain embodiments of the present invention, formulations according to this invention will exhibit about 5% or less of anhydrodaptomycin, about 5% or less of beta isomer and about 5% or less of lactone hydrolysis product, determined by HPLC analysis, after about 7 days (1 week) or longer, stored at temperatures of about 2-8° C.

In certain other embodiments of the present invention, formulations according to this invention will exhibit about 5% or less of anhydrodaptomycin, about 5% or less of beta isomer and about 5% or less of lactone hydrolysis product, determined by HPLC analysis, after about 7 days (1 week) or longer, stored at temperatures of about 25° C.

In preferred embodiments of the present invention, formulations according to this invention will exhibit about 5% or less of anhydrodaptomycin, about 5% or less of beta isomer and about 5% or less of lactone hydrolysis product, determined by HPLC analysis, wherein total impurities are no more than about 10%, determined by HPLC analysis, after about 7 days (1 week) or longer, stored at temperatures of about 2-8° C.

In certain other preferred embodiments of the present invention, formulations according to this invention will exhibit about 5% or less of anhydrodaptomycin, about 5% or less of beta isomer and about 5% or less of lactone hydrolysis product, determined by HPLC analysis, wherein total impurities are no more than about 10%, determined by HPLC analysis, after about 7 days (1 week) or longer, stored at temperatures of about 25° C.

In one embodiment of the present invention, stable and pharmaceutically acceptable liquid compositions of daptomycin comprise one or more solvents selected from polar protic solvents, and mixtures thereof.

In other embodiment of the present invention, stable and pharmaceutically acceptable liquid compositions of daptomycin comprise one or more solvents selected from polar protic solvents and polar aprotic solvents, and mixtures thereof.

Pharmaceutically acceptable polar protic solvents, according to this invention, include alkyl alcohols, ethanol, benzyl alcohol, ethylene glycol, propylene glycol, butylene glycol, glycerin, glycerol, polysorbates, for example polysorbate 20, polysorbate 40, and polysorbate 80, cyclodextrins (such as hydroxypropyl-β-cyclodextrin), polyalkylene glycols, such as polyethylene glycol (PEG), polyethylene glycol 200 (PEG 200), polyethylene glycol 300 (PEG 300), polyethylene glycol 400 (PEG 400), polyethylene glycol 600 (PEG 600), polypropylene glycol, and polybutylene glycol, and primary amides such as niacinamide.

According to the present invention, pharmaceutically acceptable polar aprotic solvents include, for example ethyl acetate, dimethyl sulfoxide (DMSO), secondary and tertiary amides, wherein secondary amides are selected from N-ethylacetamide, N-ethylformamide, and tertiary amides are selected from dimethylacetamide (DMA), N-methyl-N-vinylacetamide, N,N-dimethylpropionamide, N,N-diethylacetamide (DEA), N,N-diisopropylformamide and N,N-dimethyl formamide.

In addition, it was found that stable liquid compositions as disclosed above, can be obtained with further addition of calcium, wherein calcium in such compositions is added in the form of calcium chloride ($CaCl_2$), Ca-α-D-heptagluconate, calcium lactate or calcium acetate.

Therefore, stable and pharmaceutically acceptable liquid compositions of daptomycin according to the above described embodiments, further comprising calcium are provided.

According to the present invention, calcium is present in a molar ratio of daptomycin:calcium ranging from about 1:1 to about 1:5, such as about 1:1; about 1:2; about 1:3, about 1:4 and about 1:5.

Stable liquid compositions of daptomycin, according to any embodiment of the present invention may further comprise one or more pharmaceutically acceptable excipients, such as solubilizers, for example polyoxyl castor oil (Kolliphor® EL), polyoxyl 15 hydroxystearate (Kolliphor® HS 15), and soybean oil.

Formulations of the present invention comprise therapeutically effective amounts of daptomycin, wherein therapeutically effective amounts include concentrations ranging from about 10 mg/mL to about 120 mg/mL, such as concentration of about 10 mg/mL, about 15 mg/mL, about 20 mg/mL, about 25 mg/mL, about 30 mg/mL, about 35 mg/mL, about 40 mg/mL, about 50 mg/mL, about 60 mg/mL, about 70 mg/mL, about 80 mg/mL, about 90 mg/mL, about 100 mg/mL, about 110 mg/mL and about 120 mg/mL.

According to the present invention, method for preparing stable liquid formulations of daptomycin is provided, wherein method comprises dissolving daptomycin in one or more pharmaceutically acceptable solvents selected from the group of polar protic solvents and mixtures thereof, to form a solution.

In one aspect of the above mentioned method for preparing stable liquid formulations of daptomycin, the method further comprises adding calcium to such formed solution.

It was further found that stable liquid compositions of daptomycin can be obtained by mixing one or more polar protic solvents with one or more polar aprotic solvents.

In a further aspect of the above mentioned method of preparing stable liquid formulations of daptomycin, the method further comprises adding calcium to such formed solution.

According to the present invention, any of the above disclosed methods for preparing stable liquid compositions of daptomycin can additionally comprise adding one or more pharmaceutically acceptable excipients.

According to the present invention, disclosed formulations will typically comprise 100% or less, by volume of the formulation, of the polar protic solvent, wherein by polar protic solvent is meant one polar protic solvent, or a mixture of two or more polar protic solvents.

In one aspect of the present invention, formulations will comprise between about 30% and about 80%, by volume of the formulation, of the polar protic solvent, wherein by polar protic solvent is meant one polar protic solvent, or a mixture of two or more polar protic solvents.

According to the present invention, disclosed formulations will typically comprise 60% or less, by volume of the formulation, of the polar aprotic solvent or mixture of two or more polar aprotic solvents.

In other embodiments, formulations will comprise between about 5% and about 50%, by volume of the formulation, of the polar aprotic solvent or mixture of two or more polar aprotic solvents.

Additionally, formulations according to the present invention may comprise water to about 15% w/V, wherein content of water can be high as 15% w/V, but also can be lower than 15% w/V, such as 14%, 13%, 12%, 11%, 10%, 9%, 8%, 7%, 6%, 5%, 4%, 3%, 2%, 1% and 0.5% w/V.

According to the invention, formulations can be further diluted with diluent(s) in order to achieve lower therapeutically effective concentrations and according to the invention, the "diluent(s)" of interest herein is one which is pharmaceutically acceptable; safe and non-toxic for administration to a human, and is compatible for the preparation of a diluted formulation.

Exemplary diluents include Sterile water for injection, Bacteriostatic water for injection (BWFI), sterile saline solution (0.9% sodium chloride), Ringer's solution or dextrose solution.

For example, in a typical preparation of diluted formulations, the appropriate volume of the liquid formulation of the present invention needed for the required therapeutically effective dose can be aseptically withdrawn and transferred into an infusion bag of 0.9% sodium chloride, or of sterile water for injection or of Bacteriostatic water for injection and administrated to a patient via appropriate route of administration.

The liquid formulations of daptomycin described herein are intended to be administered via injection, for example subcutaneously, intracutaneously, intravenously, intramuscularly, intraarticularly, intrasynovially, intrasternally, intrathecally, intralesionally, intracranially or via infusion.

Also within the scope of the invention are uses of pharmaceutical formulations of daptomycin, as disclosed herein, for treating diseases caused by Gram positive bacteria such as complicated skin and soft-tissue infections (cSSTI), *Staphylococcus aureus* bloodstream infections (bacteremia), including those with right-sided infective endocarditis (RIE).

These uses comprise administering to the patient a therapeutically effective amount of formulations according to this invention or administering to the patient a therapeutically effective amount of preparation prepared from a pharmaceutical formulation of the present invention.

Embodiments encompassed by the present invention:

1. A pharmaceutical formulation comprising daptomycin, one or more polar protic solvents, and mixtures thereof.

2. A formulation according to embodiment 1, wherein one or more polar protic solvents are selected from ethanol, benzyl alcohol, 2-methyl-1-propanol, tert butyl alcohol, ethylene glycol, propylene glycol, glycerol, polysorbates, such as polysorbate 20, polysorbate 40, and polysorbate 80, polyethylene glycol (PEG), polyethylene glycol 200 (PEG 200), polyethylene glycol 300 (PEG 300), polyethylene glycol 400 (PEG 400), and polyethylene glycol 600 (PEG 600).

3. A formulation according to embodiments 1 and 2, further comprising polar aprotic solvent.

4. A formulation according to embodiment 3, wherein polar aprotic solvent is selected from ethyl acetate, dimethyl sulfoxide (DMSO), secondary and tertiary amides, wherein secondary amides are selected from N-ethylacetamide, N-ethylformamide, and tertiary amides are selected from dimethylacetamide (DMA), N-methyl-N-vinylacetamide, N,N-dimethylpropionamide, N,N-diethylacetamide (DEA), N,N-diisopropylformamide and N,N-dimethyl formamide.

5. A formulation according to any one of the above embodiments, further comprising source of calcium.

6. A formulation according to embodiment 5, wherein source of calcium is calcium chloride ($CaCl_2$)), Ca-α-D-heptagluconate, calcium lactate or calcium acetate.

7. A formulation according to embodiment 6, wherein the molar ratio of daptomycin:calcium is from about 1:1 to about 1:5.

8. A formulation according to embodiment 7, wherein the molar ratio of daptomycin:calcium is about 1:1, about 1:2, about 1:3, about 1:4 or about 1:5.

9. A formulation according to any of the above embodiments, further comprising water.

10. A formulation according to embodiment 9, wherein water is present in amount of about 15% (w/V) or less, such as 15%, 14%, 13%, 12%, 11%, 10%, 9%, 8%, 7%, 6%, 5%, 4%, 3%, 2%, 1% and 0.5% w/V.

11. A formulation according to any of the above embodiments, wherein the concentration of daptomycin is from about 10 mg/mL to about 120 mg/mL, such as concentration of about 10 mg/mL, about 15 mg/mL, about 20 mg/mL, about 25 mg/mL, about 30 mg/mL, about 35 mg/mL, about 40 mg/mL, about 50 mg/mL, about 60 mg/mL, about 70 mg/mL, about 80 mg/mL, about 90 mg/mL, about 100 mg/mL, about 110 mg/mL and about 120 mg/mL.

12. A formulation according to any of the above embodiments, wherein the concentration of one polar protic solvent or mixture of two or more polar protic solvents is from about 30% to about 80% (V/V).

13. A formulation according to any of the above embodiments, wherein the concentration of one polar aprotic or mixture of two or more polar protic solvents is less than 60% (V/V).

14. A formulation according to any of the above embodiments, wherein the concentration of one polar aprotic or mixture of two or more polar protic solvents is from about 5% to about 50%.

15. A formulation according to any of the above embodiments, further comprising one or more pharmaceutically acceptable excipients.

16. A formulation according to embodiment 9, wherein pharmaceutically acceptable excipient is a solubilizer selected from polyoxyl castor oil (Kolliphor® EL), polyoxyl 15 hydroxystearate (Kolliphor® HS 15) and soybean oil.

17. A process for preparing pharmaceutical composition of daptomycin comprising providing a solution of daptomycin according to any of the above embodiments.

18. Pharmaceutical composition of daptomycin according to any of embodiments 1-16 for use in the treatment of infections caused by Gram-positive pathogens.

EXAMPLES

Unless otherwise indicated, all experimental data and procedures described herein are obtained or performed at room temperature and atmospheric pressure.

In the Examples and tables presented below, the following abbreviations were used:
Anhydro dap—anhydrodaptomycin impurity
Beta—beta (ß-aspartyl) isomer impurity
$Ca^{2+}$—source of calcium
DAP—daptomycin
DEA—N,N-diethylacetamide
DMA—dimethylacetamide
DMSO—dimethyl sulfoxide
NA—not available
<RL—less than reporting limit of 0.05%

Example 1a, Daptomycin Stability Studies when Formulated in a Concentration of 50 Mg/mL in Solution Mixture of Polar Aprotic Solvent Dimethylacetamide and Polar Protic Solvents Selected from Ethanol, PEG 400, PEG 300, and Mixtures Thereof Daptomycin (1.354 g, given the assay on anhydrous basis of daptomycin of 95.3% and water content of 3.1%) was weighed, protected from light, into a glass beaker of 50 mL. A required amount of a polar aprotic solvent DMA was added (to make a 30% final solution) and the contents were then stirred protected from atmosphere and light using a magnetic stirrer. From the polar protic solvents, either ethanol, PEG300 or PEG400 were added to the mixture (to make a 60% final solution) while stirring protected from atmosphere and light. Finally, water was added (8%) to ensure dissolving of daptomycin while stirring (typically about 5 minutes) protected from atmosphere and light. The solution was then transferred to a volumetric flask and ethanol absolute was added to make up to volume of 25 mL. The solution was mixed to ensure homogeneity, filtered through a 0.2 μm filter, aliquoted (briefly overlaid with nitrogen to ensure an inert atmosphere) and put on stability at 2-8° C. for 7 days, protected from light.

TABLE 1A

IMPURITY PROFILES OF LIQUID COMPOSITIONS ACCORDING TO EXAMPLE 1A AT STORAGE CONDITION TEMPERATURE OF 2-8° C.

| | | Composition | | | | | | | | | |
|---|---|---|---|---|---|---|---|---|---|---|---|
| $Ca^{2+}$ | Molar ratio DAP:$Ca^{2+}$ | Solvent 1 | Solvent 2 | Water content (w/V) | Solvent 3 | Time point | Anhydro DAP | Beta | Lactone hydrolysis product | Total impurities | Appearance |
| NONE | / | DMA 30% (V/V) | / | 8% | absolute ethanol ad 25 mL | START | 0.66 | 0.05 | 0.11 | 3.5 | Clear yellow solution free of visible particles |
| | | | | | | 7 days | 1.5 | 0.05 | 0.12 | 4.6 | Clear yellow solution free of visible particles |
| NONE | / | DMA 30% (V/V) | PEG300 60% (V/V) | 8% | absolute ethanol ad 25 mL | START | 0.62 | 0.05 | 0.10 | 3.5 | Clear yellow solution free of particles |
| | | | | | | 7 days | 1.1 | 0.05 | 0.13 | 4.2 | Clear yellow solution free of visible particles |
| NONE | / | DMA 30% (V/V) | PEG400 60% (V/V) | 8% | absolute ethanol ad 25 mL | START | 0.65 | 0.06 | 0.12 | 3.6 | Clear yellow solution free of visible particles |
| | | | | | | 7 days | 1.1 | 0.06 | 0.11 | 4.0 | Clear yellow solution free of visible particles |

Results of the stability studies performed for daptomycin compositions according to Example 1a provide evidence for daptomycin stability after 7 days in view of less than 2% of anhydrodaptomycin formation, no increase of beta (ß-aspartyl) isomer impurity detected (less than 1%), as well as no significant increase (less than 1%) in lactone hydrolysis product impurity detected. Maximum total impurities are below 10%. Accordingly, compositions of Example 1a are stable at storage temperatures of 2-8° C.

Example 1b. Daptomycin Stability Studies when Formulated in a Concentration of 50 Mg/mL in Solution Mixture of Polar Aprotic Solvent Dimethylacetamide and Polar Protic Solvents Selected from Ethanol, PEG 400, PEG 300, and Mixtures Thereof with the Presence of Calcium Chloride Calcium chloride hexahydrate (5,477 g) was dissolved in 25 mL of water to provide a 1M aqueous solution of calcium chloride. Daptomycin (1.354 g, given the assay on anhydrous basis of daptomycin of 95.3% and water content of 3.1%) was weighed, protected from light, into a glass beaker of 50 mL. A required amount of a polar aprotic solvent DMA was added (30%), where applicable, followed by the required amount of polar protic solvents ethanol, PEG300 or PEG400 (60%), depending on the formulation, while stirring protected from atmosphere and light using a magnetic stirrer. Finally, a water solution of calcium chloride was added to provide 1:1 molar ratio of $Ca^{2+}$ to daptomycin (772 µL) and water to make up to 8% of total aqueous phase. The mixture was stirred to ensure dissolving of daptomycin (typically about 5 minutes), protected from atmosphere and light. The solution was then transferred to a volumetric flask and ethanol absolute was added to make up to volume of 25 mL. The solution was mixed to ensure homogeneity, filtered through a 0.2 µm filter, aliquoted (briefly overlaid with nitrogen to ensure an inert atmosphere) and put on stability at 2-8° C. for 7 days; 2 and/or 3 and/or 6 weeks; 1 and/or 2 months, protected from light and/or at 25° C. for 7 days; 2 and/or 3 weeks and/or 1 month.

TABLE 1B

IMPURITY PROFILES OF LIQUID COMPOSITIONS ACCORDING TO EXAMPLE 1B AT STORAGE CONDITION TEMPERATURE OF 2-8° C.

| | Composition | | | | | | | | | |
|---|---|---|---|---|---|---|---|---|---|---|
| $Ca^{2+}$ | Molar ratio DAP:$Ca^{2+}$ | Solvent 1 | Water content (w/V) | Solvent 2 | Time point | Anhydro DAP | Beta | Lactone hydrolysis product | Total impurities | Appearance |
| $CaCl_2$ | 1:1 | / | 8% | absolute ethanol ad 25 mL | START | 0.54 | <RL | 0.09 | 3.3 | Clear yellow solution free of visible particles |
| | | | | | 7 days | 0.58 | <RL | 0.09 | 3.4 | Clear yellow solution free of visible particles |
| | | | | | 3 weeks | 0.66 | <RL | 0.11 | 3.8 | Clear yellow solution free of visible particles |
| | | | | | 6 weeks | 0.91 | 0.06 | 0.11 | 4.8 | Clear yellow solution free of visible particles |
| | | | | | 2 months | 1.1 | 0.05 | 0.12 | 5.2 | Clear yellow solution free of visible particles |
| $CaCl_2$ | 1:1 | DMA 30% (V/V) | 8% | absolute ethanol ad 25 mL | START | NA | NA | NA | NA | NA |
| | | | | | 7 days | 0.63 | 0.05 | 0.1 | 3.6 | Clear yellow solution free of visible particles |
| | | | | | 14 days | 0.67 | 0.05 | 0.11 | 3.6 | Clear yellow solution free of visible particles |
| | | | | | 1 month | 0.76 | <RL | 0.11 | 3.7 | Clear yellow solution free of visible particles |
| | | | | | 2 months | 1.1 | 0.05 | 0.13 | 4.3 | Clear yellow solution free of visible particles |

Results of the stability studies performed for daptomycin compositions according to Example 1b provide evidence for daptomycin stability after 2 months in view of less than 2% of anhydrodaptomycin formation, no increase of beta (ß-aspartyl) isomer impurity detected (less than 1%), as well as no significant increase (less than 1%) in lactone hydrolysis product impurity detected. Maximum total impurities are below 10%.

Accordingly, compositions of Example 1b are stable at storage temperatures of 2-8° C.

TABLE 1B

| | Composition | | | | | | | | | | |
|---|---|---|---|---|---|---|---|---|---|---|---|
| $Ca^{2+}$ | Molar ratio DAP:$Ca^{2+}$ | Solvent 1 | Solvent 2 | Water content (w/V) | Solvent 3 | Time point | Anhydro DAP | Beta | Lactone hydrolysis product | Total impurities | Appearance |
| $CaCl_2$ | 1:1 | / | PEG400 60% (V/V) | 8% | absolute ethanol ad 25 mL | START | 0.56 | <RL | 0.09 | 3.3 | Clear yellow solution free of visible particles |
| | | | | | | 1 month | 0.73 | <RL | 0.12 | 3.7 | Clear yellow solution free of visible particles |
| $CaCl_2$ | 1:1 | DMA 30% (V/V) | PEG400 60% (V/V) | 8% | absolute ethanol ad 25 mL | START | NA | NA | NA | NA | NA |
| | | | | | | 7 days | 0.6 | 0.05 | 0.1 | 3.5 | Clear yellow solution free of visible particles |
| | | | | | | 14 days | 0.59 | 0.05 | 0.11 | 3.5 | Clear yellow solution free of visible particles |
| | | | | | | 1 month | 0.6 | <RL | 0.11 | 3.4 | Clear yellow solution free of visible particles |
| | | | | | | 2 months | 0.81 | 0.05 | 0.12 | 3.7 | Clear yellow solution free of visible particles |
| $CaCl_2$ | 1:1 | DMA 30% (V/V) | PEG300 60% (V/V) | 8% | absolute ethanol ad 25 mL | START | 0.54 | 0.06 | 0.11 | 3.4 | Clear yellow solution free of visible particles |
| | | | | | | 7 days | 0.6 | 0.05 | 0.1 | 3.4 | Clear yellow solution free of visible particles |
| | | | | | | 14 days | 0.63 | 0.05 | 0.1 | 3.5 | Clear yellow solution free of visible particles |
| | | | | | | 1 month | 0.68 | <RL | 0.11 | 3.5 | Clear yellow solution free of visible particles |
| | | | | | | 2 months | 0.92 | 0.05 | 0.13 | 3.9 | Clear yellow solution free of visible particles |

Results of the stability studies performed for daptomycin compositions according to Example 1b, shown in Table 1b-continued, provide further evidence for daptomycin stability after 2 months in view of less than 1% anhydrodaptomycin formation, no increase of beta (ß-aspartyl) isomer (less than 1%) detected, as well as no significant detected increase in lactone hydrolysis product impurity. Maximum total impurities are below 5%.

Accordingly, compositions of Example 1b are stable at storage temperatures of 2-8° C.

TABLE 1C

IMPURITY PROFILES OF LIQUID COMPOSITIONS ACCORDING TO EXAMPLE 1B AT STORAGE CONDITION TEMPERATURE OF 25° C./60% RH

| | | Composition | | | | | | | | | |
|---|---|---|---|---|---|---|---|---|---|---|---|
| $Ca^{2+}$ | Molar ratio DAP:$Ca^{2+}$ | Solvent 1 | Solvent 2 | Water content (w/V) | Solvent 3 | Time point | Anhydro DAP | Beta | Lactone hydrolysis product | Total impurities | Appearance |
| $CaCl_2$ | 1:1 | / | / | 8% | absolute ethanol ad 25 mL | START | 0.54 | <RL | 0.09 | 3.3 | Clear yellow solution free of visible particles |
| | | | | | | 7 DAYS | 1.1 | 0.06 | 0.11 | 4.7 | Clear yellow solution free of visible particles |
| | | | | | | 3 W | 2.2 | 0.09 | 0.15 | 7.7 | Clear yellow solution free of visible particles |
| $CaCl_2$ | 1:1 | / | PEG400 60% (V/V) | 8% | absolute ethanol ad 25 mL | START | 0.56 | <RL | 0.09 | 3.3 | Clear yellow solution free of visible particles |
| | | | | | | 7 DAYS | 1.2 | 0.06 | 0.13 | 4.7 | Clear yellow solution free of visible particles |
| | | | | | | 1 M | 2.8 | <RL | 0.17 | 7.8 | Clear yellow solution free of visible particles |
| $CaCl_2$ | 1:1 | DMA 30% (V/V) | PEG400 60% (V/V) | 8% | absolute ethanol ad 25 mL | START | 0.65 | <RL | 0.11 | 3.5 | Clear yellow solution free of visible particles |
| | | | | | | 7 DAYS | 0.98 | 0.05 | 0.12 | 4.1 | Clear yellow solution free of visible particles |
| | | | | | | 14 DAYS | 1.4 | 0.07 | 0.14 | 4.7 | Clear yellow solution free of visible particles |
| $CaCl_2$ | 1:1 | DMA 30% (V/V) | PEG400 60% (V/V) | 8% | absolute ethanol ad 25 mL | START | NA | NA | NA | NA | NA |
| | | | | | | 1 M | 2.3 | 0.08 | 0.17 | 6.8 | Clear yellow solution free of visible particles |
| $CaCl_2$ | 1:1 | DMA 30% (V/V) | PEG300 60% (V/V) | 8% | absolute ethanol ad 25 mL | START | 0.54 | 0.06 | 0.11 | 3.4 | Clear yellow solution free of visible particles |
| | | | | | | 7 DAYS | 1.2 | 0.06 | 0.12 | 4.4 | Clear yellow solution free of visible particles |
| | | | | | | 14 DAYS | 1.7 | 0.06 | 0.13 | 4.9 | Clear yellow solution free of visible particles |
| | | | | | | 1 M | 2.9 | 0.10 | 0.18 | 6.6 | Clear yellow solution free of visible particles |

Results of the stability studies performed for daptomycin compositions according to Example 1c provide evidence for daptomycin stability after 3 weeks.

Accordingly, compositions of Example 1c are stable at storage temperatures of 25° C./60% RH.

Example 2. Daptomycin Stability Studies when Formulated in a Concentration of 50 Mg/mL in Solution Mixture of Kolliphor® EL and Polar Protic Solvents Selected from Ethanol, Benzyl Alcohol, and Mixtures Thereof with the Presence of Calcium Chloride Calcium chloride hexahydrate (169 mg) was dissolved in a required mass of absolute ethanol (5.925 g or 3.358 g, respectively) in a glass beaker by stirring using a magnetic stirrer protected from atmosphere until the dissolution of calcium chloride hexahydrate. The required amount of daptomycin was weighed protected from light and added (1.354 g, given the assay on anhydrous basis of daptomycin of 95.3% and water content of 3.1%) to the calcium chloride hexahydrate solution in ethanol and the contents of the beaker was stirred protected from light and atmosphere. Water was added to the mixture to ensure dissolving of daptomycin (1 g) and the mixture was stirred protected from light and atmosphere. The required amount of either Kolliphor® EL (16.25 mL) or Kolliphor EL® (16.25 mL) solution with benzyl alcohol (4.5 mL) was then added to the daptomycin solution. The solution was stirred, protected from the environment (light and atmosphere), and then transferred to a volumetric flask and water was added to make up to volume of 25 mL. The solution was mixed to ensure homogeneity, filtered through a 0.2 µm filter, aliquoted (briefly overlaid with nitrogen to ensure an inert atmosphere) and put at 2-8° C. for 7 days and 5 months and at 25° C. for 7 days, protected from light.

As visible from results of the stability studies performed for daptomycin compositions according to Example 2 presented below, compositions of Example 2 are stable at storage temperatures of 2-8° C. and of 25° C./60% RH.

TABLE 2A

IMPURITY PROFILES OF LIQUID COMPOSITIONS ACCORDING TO EXAMPLE 2 AT STORAGE CONDITION TEMPERATURE OF 2-8° C.

| | Composition | | | | | | | | | |
|---|---|---|---|---|---|---|---|---|---|---|
| $Ca^{2+}$ | Molar ratio DAP:$Ca^{2+}$ | Solubi-lizer | Solvent 1 | Solvent 2 | Water content (w/V) | Time point | Anhydro DAP | Beta | Lactone hydrolysis product | Total impurities | Appearance |
| $CaCl_2$ | 1:1 | Kolliphor EL 65% (V/V) | absolute ethanol 30% (w/V) | / | ultrapure water ad 25 mL (ca. 5% w/V) | START | 0.59 | <RL | 0.1 | 3.4 | Clear yellow solution free of visible particles |
| | | | | | | 14 days | 0.75 | <RL | 0.11 | 3.7 | Clear yellow solution free of visible particles |
| | | | | | | 5 months | 2.4 | 0.05 | 0.18 | 6.0 | Clear yellow solution free of visible particles |
| $CaCl_2$ | 1:1 | Kolliphor EL 65% (V/V) | absolute ethanol 17% (w/V) | benzyl alcohol 18% (V/V) | ultrapure water ad 25 mL (ca. 5% w/V) | START | 0.59 | <RL | 0.11 | 3.5 | Clear yellow solution free of visible particles |
| | | | | | | 14 days | 0.64 | 0.05 | 0.09 | 3.5 | Clear yellow solution free of visible particles |
| | | | | | | 5 months | 1.2 | <RL | 0.13 | 4.6 | Clear yellow solution free of visible particles |

TABLE 2B

IMPURITY PROFILES OF LIQUID COMPOSITIONS ACCORDING TO EXAMPLE 2 AT STORAGE CONDITION TEMPERATURE OF 25° C./60% RH

| | Composition | | | | | | | | | |
|---|---|---|---|---|---|---|---|---|---|---|
| $Ca^{2+}$ | Molar ratio DAP:$Ca^{2+}$ | Solubi-lizer | Solvent 1 | Solvent 2 | Water content (w/V) | Time point | Anhydro DAP | Beta | Lactone hydrolysis product | Total impurities | Appearance |
| $CaCl_2$ | 1:1 | Kolliphor EL 65% (V/V) | absolute ethanol 30% (w/V) | / | ultrapure water ad 25 mL (ca. 5% w/V) | START | 0.59 | <RL | 0.10 | 3.4 | Clear yellow solution free of visible particles |
| | | | | | | 7 DAYS | 1.8 | 0.07 | 0.16 | 5.3 | Clear yellow solution free of visible particles |
| $CaCl_2$ | 1:1 | Kolliphor EL 65% (V/V) | absolute ethanol 17% (w/V) | benzyl alcohol 18% (V/V) | ultrapure water ad 25 mL (ca. 5% w/V) | START | 0.59 | <RL | 0.11 | 3.5 | Clear yellow solution free of visible particles |
| | | | | | | 7 DAYS | 1.2 | 0.06 | 0.13 | 4.5 | Clear yellow solution free of visible particles |

Example 3. Daptomycin Stability Studies when Formulated in a Concentration of 50 Mg/mL in Solution Mixture of Polar, Aprotic Solvents Selected from N,N-Diethylacetamide (DEA), N-Ethylacetamide and N,N-Dimethylpropionamide and Polar Protic Solvent Ethanol with the Presence of Calcium Chloride Daptomycin (1.354 g, given the assay on anhydrous basis of daptomycin of 95.3% and water content of 3.1%) was weighed, protected from light, into a glass beaker of 50 mL. A required amount of a polar aprotic solvent DEA, N-ethylacetamide or N,N-dimethylpropionamide was added (30%) to the beaker, followed by absolute ethanol, 1M aqueous solution of calcium chloride (772 μL) and water (228 μL) and the contents were then stirred protected from atmosphere and light using a magnetic stirrer until daptomycin was dissolved (typically around 5 minutes). The solution was then transferred to a volumetric flask and absolute ethanol was added to make up to volume of 25 mL. The solution was mixed to ensure homogeneity, filtered through a 0.2 μm filter, aliquoted (briefly overlaid with nitrogen to ensure an inert atmosphere) and put either at 2-8° C. for 7 days, 2, 3, 4 and/or 6 weeks protected from light or at 25° C. for 7 days, 3 and/or 6 weeks protected from light.

As visible from results presented below, compositions of Example 3 are stable at storage condition temperature of 2-8° C., as well as at 25° C./60% RH for more than 7 days.

TABLE 3A

IMPURITY PROFILES OF LIQUID COMPOSITIONS ACCORDING TO EXAMPLE 3 AT STORAGE CONDITION TEMPERATURE OF 2-8° C.

| | Composition | | | | | | | | | |
|---|---|---|---|---|---|---|---|---|---|---|
| $Ca^{2+}$ | Molar ratio DAP:$Ca^{2+}$ | Solvent 1 | Water content (w/V) | Solvent 2 | Time point | Anhydro DAP | Beta | Lactone hydrolysis product | Total impurities | Appearance |
| $CaCl_2$ | 1:1 | DEA 30% (V/V) | 8% | absolute ethanol ad 25 mL | START | 0.55 | <RL | 0.10 | 3.4 | Clear yellow solution free of visible particles |
| | | | | | 7 days | 0.58 | <RL | 0.1 | 3.4 | Clear yellow solution free of visible particles |
| | | | | | 3 weeks | 0.64 | <RL | 0.11 | 3.6 | Clear yellow solution free of visible particles |
| | | | | | 6 weeks | 0.78 | <RL | 0.11 | 4.4 | Clear yellow solution free of visible particles |
| | | | | | 2 months | 1.1 | <RL | 0.11 | 4.6 | Clear yellow solution free of visible particles |
| $CaCl_2$ | 1:1 | N-ethylacetamide 30% (V/V) | 8% | absolute ethanol ad 25 mL | START | 0.57 | <RL | 0.11 | 3.3 | Clear yellow solution free of visible particles |
| | | | | | 7 days | 0.67 | <RL | 0.11 | 3.5 | Clear yellow solution free of visible particles |
| $CaCl_2$ | 1:1 | N,N-dimethylpropionamide 30% (V/V) | 8% | absolute ethanol ad 25 mL | START | 0.73 | <RL | 0.09 | 3.5 | Clear yellow solution free of visible particles |
| | | | | | 7 days | NA | NA | NA | NA | Clear yellow solution free of visible particles |
| | | | | | 14 days | NA | NA | NA | NA | Clear yellow solution free of visible particles |
| | | | | | 1 month | 0.71 | <RL | 0.11 | 3.8 | Clear yellow solution free of visible particles |

TABLE 3B

IMPURITY PROFILES OF LIQUID COMPOSITIONS ACCORDING TO EXAMPLE 3 AT STORAGE CONDITION TEMPERATURE OF 25° C./60% RH

| | Composition | | | | | | | | | |
|---|---|---|---|---|---|---|---|---|---|---|
| $Ca^{2+}$ | Molar ratio DAP:$Ca^{2+}$ | Solvent 1 | Water content (w/V) | Solvent 2 | Time point | Anhydro DAP | Beta | Lactone hydrolysis product | Total impurities | Appearance |
| $CaCl_2$ | 1:1 | DEA 30% (V/V) | 8% | absolute ethanol ad 25 mL | START | 0.55 | <RL | 0.1 | 3.4 | Clear yellow solution free of visible particles |
| | | | | | 7 DAYS | 0.89 | <RL | 0.12 | 4.3 | Clear yellow solution free of visible particles |
| | | | | | 3 W | 1.5 | <RL | 0.13 | 6 | Clear yellow solution free of visible particles |
| | | | | | 6 W | 2.4 | 0.1 | 0.14 | 8.5 | Clear yellow solution free of visible particles |
| $CaCl_2$ | 1:1 | N-ethylacetamide 30% (V/V) | 8% | absolute ethanol ad 25 mL | START | 0.57 | <RL | 0.11 | 3.3 | Clear yellow solution free of visible particles |
| | | | | | 7 DAYS | 1.5 | 0.06 | 0.12 | 5.1 | Clear yellow solution free of visible particles |
| $CaCl_2$ | 1:1 | N,N-dimethylpropionamide 30% (V/V) | 8% | absolute ethanol ad 25 mL | START | 0.73 | <RL | 0.09 | 3.5 | Clear yellow solution free of visible particles |
| | | | | | 7 DAYS | 1.3 | 0.07 | 0.13 | 4.8 | Clear yellow solution free of visible particles |

TABLE 3B-continued

IMPURITY PROFILES OF LIQUID COMPOSITIONS ACCORDING TO EXAMPLE 3 AT STORAGE CONDITION TEMPERATURE OF 25° C./60% RH

| | Composition | | | | | | | | | |
|---|---|---|---|---|---|---|---|---|---|---|
| $Ca^{2+}$ | Molar ratio DAP:$Ca^{2+}$ | Solvent 1 | Water content (w/V) | Solvent 2 | Time point | Anhydro DAP | Beta | Lactone hydrolysis product | Total impurities | Appearance |
| | | | | | 1 M | 2.8 | 0.09 | 0.17 | 7.6 | Clear yellow solution free of visible particles |

Example 4. Daptomycin Stability Studies when Formulated in a Concentration of 50 Mg/mL in Various Solution Mixtures of Polar Aprotic Solvents and/or Polar Protic Solvents with the Presence of Calcium Chloride in Different Molar Ratios to Daptomycin and Additionally when Solubilizer is Present Calcium chloride hexahydrate (5,477 g) was dissolved in 25 mL of water to provide a 1M aqueous solution of calcium chloride. Daptomycin (1.354 g, given the assay on anhydrous basis of daptomycin of 95.3% and water content of 3.1%) was weighed, protected from light, into a glass beaker of 50 mL. A required amount of a polar aprotic solvent DMA was added (7.5 mL or 1.5 mL) to the beaker, where required, and the contents of the beaker were stirred using a magnetic stirrer protected from light and atmosphere. Where required, PEG400 (20.0 mL) was added to the solution, followed by the addition of 1M calcium chloride aqueous solution (772 or 1544 μL) and water (1228 or 456 μL) and the contents were stirred protected from atmosphere and light using a magnetic stirrer until daptomycin was dissolved (typically around 5 minutes). The solution was then transferred to a volumetric flask and absolute ethanol was added to make up to volume of 25 mL. The solution was mixed to ensure homogeneity, filtered through a 0.2 μm filter, aliquoted (briefly overlaid with nitrogen to ensure an inert atmosphere) and put either at 25° C. for 7 days and 14 days, where applicable, protected from light.

Alternatively, the solutions with Kolliphor® HS 15 were prepared in the following way: A required mass of Kolliphor® HS 15 (12.5 g) was weighed into a 50 mL glass beaker and dissolved in absolute ethanol (11.628 g) by stirring protected from atmosphere and light using a magnetic stirrer. Following, the solution of Kolliphor® HS 15 in ethanol was added to the weighed amount of daptomycin (1.354 g, given the assay on anhydrous basis of daptomycin of 95.3% and water content of 3.1%). Following, calcium chloride hexahydrate was added (169 mg) and water (1 mL) and contents were stirred protected from atmosphere and light, using a magnetic stirrer, until the dissolution of all solid substances. The solution was then transferred to a volumetric flask and, where applicable, soybean oil was added (0.1 mL) and the volume was made up to 25 mL using either water or absolute ethanol. The solution was mixed to ensure homogeneity, filtered through a 0.2 μm filter, aliquoted (briefly overlaid with nitrogen to ensure an inert atmosphere) and put either at 25° C. for 7 days and 14 days, where applicable, protected from light.

Finally, solutions of daptomycin in ethanol were prepared in the following way: Absolute ethanol was weighed in a glass beaker of 50 mL (around 10 g) and calcium chloride hexahydrate (169 mg) was added to it and dissolved by stirring, using a magnetic stirrer, protected from atmosphere (typically around 5 minutes). Daptomycin (1.354 g) was added, followed by addition of water (1 or 2 mL), while stirring protected from light and atmosphere. The solution was then transferred to a volumetric flask and the volume was made up to 25 mL using absolute ethanol. The solution was mixed to ensure homogeneity, filtered through a 0.2 μm filter, aliquoted (briefly overlaid with nitrogen to ensure an inert atmosphere) and put either at 25° C. for 7 days, protected from light.

TABLE 4

IMPURITY PROFILES OF LIQUID COMPOSITIONS ACCORDING TO EXAMPLE 4 AT STORAGE CONDITION TEMPERATURE OF 25° C./60% RH

| | Composition | | | | | | | | | |
|---|---|---|---|---|---|---|---|---|---|---|
| $Ca^{2+}$ | Molar ratio DAP:$Ca^{2+}$ | Solvent 1 or Solubilizer 1 | Solvent 2 or Solubilizer 2 | Water content (w/V) | Solvent 3 | Time point | Anhydro DAP | Beta | Lactone hydrolysis product | Total impurities | Appearance |
| / | / | / | / | 10.8% | absolute ethanol ad 25 mL | START | 0.98 | 0.05 | 0.10 | 3.9 | Clear yellow solution free of visible particles |
| | | | | | | 7 DAYS | 10.7 | 0.28 | 0.24 | 17.1 | Clear yellow solution free of visible particles |
| $CaCl_2$ | 1:1 | / | / | 4% | absolute ethanol ad 25 mL | START | 0.58 | <RL | 0.09 | 3.3 | Clear yellow solution free of visible particles |
| | | | | | | 7 DAYS | 0.73 | 0.05 | 0.10 | 4.4 | Clear yellow solution free of visible particles |

TABLE 4-continued

IMPURITY PROFILES OF LIQUID COMPOSITIONS ACCORDING TO EXAMPLE 4 AT STORAGE CONDITION TEMPERATURE OF 25° C./60% RH

| Ca$^{2+}$ | Molar ratio DAP:Ca$^{2+}$ | Solvent 1 or Solubilizer 1 | Solvent 2 or Solubilizer 2 | Water content (w/V) | Solvent 3 | Time point | Anhydro DAP | Beta | Lactone hydrolysis product | Total impurities | Appearance |
|---|---|---|---|---|---|---|---|---|---|---|---|
| CaCl$_2$ | 1:1 | / | / | 8% | absolute ethanol ad 25 mL | START | 0.55 | <RL | 0.09 | 3.3 | Clear yellow solution free of visible particles |
|  |  |  |  |  |  | 7 DAYS | 1.2 | 0.08 | 0.12 | 5.1 | Clear yellow solution free of visible particles |
| CaCl$_2$ | 1:1 | DMA 30% (V/V) | / | 8% | absolute ethanol ad 25 mL | START | 0.67 | 0.05 | 0.1 | 3.5 | Clear yellow solution free of visible particles |
|  |  |  |  |  |  | 7 DAYS | 1.1 | 0.06 | 0.12 | 4.5 | Clear yellow solution free of visible particles |
|  |  |  |  |  |  | 14 DAYS | 1.7 | 0.08 | 0.14 | 5.5 | Clear yellow solution free of visible particles |
| CaCl$_2$ | 1:2 | ethyl acetate 15% (V/V) | / | 8% | absolute ethanol ad 25 mL | START | 0.59 | 0.05 | 0.10 | 3.8 | Clear yellow solution free of visible particles |
|  |  |  |  |  |  | 7 DAYS | 0.64 | 0.06 | 0.09 | 4.8 | Clear yellow solution free of visible particles |
| CaCl$_2$ | 1:2 | DMSO 30% (V/V) | / | 8% | absolute ethanol ad 25 mL | START | 0.61 | 0.05 | 0.09 | 3.8 | Clear yellow solution free of visible particles |
|  |  |  |  |  |  | 7 DAYS | 0.85 | 0.07 | 0.10 | 4.4 | Clear yellow solution free of visible particles |
| CaCl$_2$ | 1:2 | DMA 6% (V/V) | PEG400 80% (V/V) | 8% | absolute ethanol ad 25 mL | START | 0.61 | 0.06 | 0.11 | 3.7 | Clear yellow solution free of visible particles |
|  |  |  |  |  |  | 7 DAYS | 0.79 | 0.08 | 0.13 | 4.6 | Clear yellow solution free of visible particles |
|  |  |  |  |  |  | 1 M | 1.2 | 0.06 | 0.25 | 9.6 | Clear yellow solution free of visible particles |
| CaCl$_2$ | 1:1 | DMA 6% (V/V) | PEG400 80% (V/V) | 8% | absolute ethanol ad 25 mL | START | 0.65 | 0.07 | 0.12 | 3.8 | Clear yellow solution free of visible particles |
|  |  |  |  |  |  | 7 DAYS | 1.1 | 0.08 | 0.13 | 4.5 | Clear yellow solution free of visible particles |
|  |  |  |  |  |  | 1 M | 2.7 | 0.08 | 0.19 | 8.3 | Clear yellow solution free of visible particles |
| CaCl$_2$ | 1:2 | / | PEG400 80% (V/V) | 8% | absolute ethanol ad 25 mL | START | 0.64 | 0.05 | 0.11 | 3.7 | Clear yellow solution free of visible particles |
|  |  |  |  |  |  | 7 DAYS | 0.8 | 0.05 | 0.14 | 4.6 | Clear yellow solution free of visible particles |
|  |  |  |  |  |  | 1 M | 1.1 | 0.07 | 0.20 | 7.5 | Clear yellow solution free of visible particles |
| CaCl$_2$ | 1:1 | Kolliphor HS 15 50% (w/V) | ethanol 46.5% (w/V) | ultrapure water ad 25 mL (ca. 12% w/V) | / | START | 0.56 | <RL | 0.08 | 3.4 | Clear yellow solution free of visible particles |
|  |  |  |  |  |  | 7 DAYS | 1.5 | 0.07 | 0.12 | 5.1 | Clear yellow solution free of visible particles |
| CaCl$_2$ | 1:1 | Kolliphor HS 15 50% (w/V) | 0.4% soybean oil (V/V) | 4% | absolute ethanol ad 25 mL | START | 0.54 | 0.05 | 0.09 | 3.4 | Clear yellow solution free of visible particles |
|  |  |  |  |  |  | 7 DAYS | 1.4 | 0.05 | 0.12 | 5.1 | Clear yellow solution free of visible particles |
| CaCl$_2$ | 1:1 | glycerol 15% (V/V) | / | 8% | absolute ethanol ad 25 mL | START | 0.6 | 0.06 | 0.10 | 3.6 | Clear yellow solution free of visible particles |

TABLE 4-continued

IMPURITY PROFILES OF LIQUID COMPOSITIONS ACCORDING TO EXAMPLE 4 AT STORAGE CONDITION TEMPERATURE OF 25° C./60% RH

| | Composition | | | | | | | | | | |
|---|---|---|---|---|---|---|---|---|---|---|---|
| $Ca^{2+}$ | Molar ratio DAP:$Ca^{2+}$ | Solvent 1 or Solubilizer 1 | Solvent 2 or Solubilizer 2 | Water content (w/V) | Solvent 3 | Time point | Anhydro DAP | Beta | Lactone hydrolysis product | Total impurities | Appearance |
| | | | | | | 7 DAYS | 2.3 | 0.07 | 0.14 | 6.4 | Clear yellow solution free of visible particles |
| $CaCl_2$ | 1:1 | glycerol 15% (V/V) | PEG400 60% (V/V) | 14% | absolute ethanol ad 25 mL | START | 0.62 | 0.05 | 0.11 | 3.5 | Clear yellow solution free of visible particles |
| | | | | | | 7 DAYS | 2.7 | 0.08 | 0.17 | 6.5 | Clear yellow solution free of visible particles |
| $CaCl_2$ | 1:1 | N-ethylformamide 30% (V/V) | / | 8% | absolute ethanol ad 25 mL | START | 0.63 | 0.05 | 0.12 | 3.7 | Clear yellow solution free of visible particles |
| | | | | | | 7 DAYS | 2.7 | 0.08 | 0.15 | 7.3 | Clear yellow solution free of visible particles |

Example 5. Daptomycin Stability Studies when Formulated in a Concentration of 50 Mg/mL in Various Solution Mixtures of Polar Aprotic Solvents and/or Polar Erotic Solvents with the Presence of Calcium Chloride in Different Molar Ratios to Daptomycin and Additionally when Solubilizer is Present at Storage Condition Temperatures of 40° C./75% RH In addition, daptomycin stability in liquid compositions according to this invention was evaluated when exposed to elevated temperatures of 40° C./75% RH, and such formulations exhibit to be both chemically and physically stabile.

TABLE 5

IMPURITY PROFILES OF LIQUID COMPOSITIONS ACCORDING TO EXAMPLE 5 AT STORAGE CONDITION TEMPERATURE OF 40° C./75% RH

| | Composition | | | | | | | | | | |
|---|---|---|---|---|---|---|---|---|---|---|---|
| $Ca^{2+}$ | Molar ratio DAP:$Ca^{2+}$ | Solvent 1 or Solubilizer | Solvent 2 | Water content (w/V) | Solvent 3 | Time point | Anhydro DAP | Beta | Lactone hydrolysis product | Total impurities | Appearance |
| $CaCl_2$ | 1:2 | DMA 6% (V/V) | PEG400 80% (V/V) | 8% | absolute ethanol ad 25 mL | START | 0.56 | <RL | 0.10 | 3.4 | Clear yellow solution free of visible particles |
| | | | | | | 1 DAY | 0.67 | <RL | 0.12 | 4.2 | Clear yellow solution free of visible particles |
| $CaCl_2$ | 1:2 | / | PEG400 80% (V/V) | 8% | absolute ethanol ad 25 mL | START | 0.55 | <RL | 0.11 | 3.4 | Clear yellow solution free of visible particles |
| | | | | | | 1 DAY | 0.69 | <RL | 0.12 | 4.1 | Clear yellow solution free of visible particles |
| $CaCl_2$ | 1:2 | polysorbate 80 30% (V/V) | / | 8% | absolute ethanol ad 25 mL | START | 0.56 | 0.06 | 0.1 | 3.5 | Clear yellow solution free of visible particles |
| | | | | | | 1 DAY | 0.65 | 0.07 | 0.11 | 4.6 | Clear yellow solution free of visible particles |
| $CaCl_2$ | 1:2 | polysorbate 20 30% (V/V) | / | 8% | absolute ethanol ad 25 mL | START | 0.55 | 0.05 | 0.11 | 3.5 | Clear yellow solution free of visible particles |
| | | | | | | 1 DAY | 0.66 | 0.05 | 0.12 | 4.8 | Clear yellow solution free of visible particles |

TABLE 5-continued

IMPURITY PROFILES OF LIQUID COMPOSITIONS ACCORDING TO EXAMPLE 5 AT STORAGE CONDITION TEMPERATURE OF 40° C./75% RH

| | | Composition | | | | | | | | | |
|---|---|---|---|---|---|---|---|---|---|---|---|
| $Ca^{2+}$ | Molar ratio DAP:$Ca^{2+}$ | Solvent 1 or Solubilizer | Solvent 2 | Water content (w/V) | Solvent 3 | Time point | Anhydro DAP | Beta | Lactone hydrolysis product | Total impurities | Appearance |
| $CaCl_2$ | 1:2 | / | PEG600 60% (V/V) | 8% | absolute ethanol ad 25 mL | START | 0.54 | <RL | 0.10 | 3.3 | Clear yellow solution free of visible particles |
| | | | | | | 1 DAY | 0.61 | 0.05 | 0.11 | 4.2 | Clear yellow solution free of visible particles |
| $CaCl_2$ | 1:2 | / | propylene glycol 60% (V/V) | 8% | absolute ethanol ad 25 mL | START | 0.58 | 0.05 | 0.11 | 3.4 | Clear yellow solution free of visible particles |
| | | | | | | 1 DAY | 1.6 | 0.06 | 0.11 | 4.9 | Clear yellow solution free of visible particles |
| $CaCl_2$ | 1:2 | / | 2-methyl-1-propanol (isobutanol) 15% (V/V) | 8% | absolute ethanol ad 25 mL | START | 0.58 | 0.06 | 0.10 | 3.4 | Clear yellow solution free of visible particles |
| | | | | | | 1 DAY | 0.62 | 0.06 | 0.11 | 4.4 | Clear yellow solution free of visible particles |
| $CaCl_2$ | 1:2 | / | / | 8% | absolute ethanol ad 25 mL | START | 0.64 | 0.06 | 0.10 | 3.6 | Clear yellow solution free of visible particles |
| | | | | | | 1 DAY | 0.78 | 0.07 | 0.11 | 4.7 | Clear yellow solution free of visible particles |
| $CaCl_2$ | 1:2 | / | PEG200 60% (V/V) | 8% | absolute ethanol ad 25 mL | START | 0.58 | 0.05 | 0.09 | 3.8 | Clear yellow solution free of visible particles |
| | | | | | | 1 DAY | 1.4 | 0.08 | 0.11 | 5.0 | Clear yellow solution free of visible particles |
| $CaCl_2$ | 1:2 | / | ethylene glycol 60% (V/V) | 8% | absolute ethanol ad 25 mL | START | 0.65 | <RL | 0.11 | 3.6 | Clear yellow solution free of visible particles |
| | | | | | | 1 DAY | 2.3 | 0.06 | 0.13 | 6.0 | Clear yellow solution free of visible particles |
| $CaCl_2$ | 1:2 | / | PEG300 60% (V/V) | 8% | absolute ethanol ad 25 mL | START | 0.64 | <RL | 0.11 | 3.5 | Clear yellow solution free of visible particles |
| | | | | | | 1 DAY | 0.82 | <RL | 0.12 | 4.0 | Clear yellow solution free of visible particles |
| $CaCl_2$ | 1:2 | / | PEG400 60% (V/V) | 8% | absolute ethanol ad 25 mL | START | 0.61 | <RL | 0.11 | 3.4 | Clear yellow solution free of visible particles |
| | | | | | | 1 DAY | 0.68 | <RL | 0.10 | 3.8 | Clear yellow solution free of visible particles |
| $CaCl_2$ | 1:2 | Kolliphor HS15 60% (V/V) | / | 8% | absolute ethanol ad 25 mL | START | 0.64 | <RL | 0.10 | 3.4 | Clear yellow solution free of visible particles |
| | | | | | | 1 DAY | 0.80 | 0.05 | 0.11 | 4.0 | Clear yellow solution free of visible particles |
| $CaCl_2$ | 1:2 | Kolliphor EL 60% (V/V) | / | 8% | absolute ethanol ad 25 mL | START | 0.63 | <RL | 0.11 | 3.5 | Clear yellow solution free of visible particles |
| | | | | | | 1 DAY | 0.89 | 0.05 | 0.12 | 4.1 | Clear yellow solution free of visible particles |
| $CaCl_2$ | 1:2 | / | tertbutyl alcohol 15% (V/V) | 8% | absolute ethanol ad 25 mL | START | 0.63 | 0.05 | 0.12 | 3.7 | Clear yellow solution free of visible particles |
| | | | | | | 1 DAY | 0.70 | 0.07 | 0.11 | 4.8 | Clear yellow solution free of visible particles |

Example 6. Daptomycin Stability Studies when Formulated in a Concentration of 120 Mg/mL in Various Solution Mixtures of Polar Aprotic Solvents and/or Polar Protic Solvents with the Presence of Calcium Chloride in Different Molar Ratios to Daptomycin and Additionally in the Presence of Solubilizer Additionally, daptomycin stability in liquid compositions according to this invention was evaluated at higher concentrations of daptomycin and in view of stability evaluation and comparison at different storage conditions.

From the below presented results, it is evident that the rate of impurities formation, when formulations of the present invention are exposed to elevated temperatures of 40° C./75% RH, refrigerated conditions of 2-8° C. and room temperature condition of 25° C./60% RH are comparable and such formulations exhibit to be both chemically and physically stabile.

TABLE 6

IMPURITY PROFILES OF LIQUID COMPOSITIONS ACCORDING TO EXAMPLE 6 AT DIFFERENT STORAGE CONDITION TEMPERATURE

| Ca$^{2+}$ | Molar ratio DAP:Ca$^{2+}$ | Solvent 1 | Solvent 2 | Water content (w/V) | Solvent 3 | Time point/ Temperature | Anhydro DAP | Beta | Lactone hydrolysis product | Total impurities | Appearance |
|---|---|---|---|---|---|---|---|---|---|---|---|
| CaCl$_2$ | 1:1 | / | / | 8% | absolute ethanol ad 25 mL | START | 0.58 | 0.05 | 0.09 | 3.8 | Clear yellow solution free of visible particles |
| | | | | | | 1 DAY/ 40° C. | 1.2 | 0.09 | 0.11 | 5.2 | Clear yellow solution free of visible particles |
| | | | | | | 7 DAYS/ 2-8° C. | 0.63 | 0.05 | 0.10 | 3.8 | Clear yellow solution free of visible particles |
| | | | | | | 7 DAYS/ 25° C. | 1.1 | 0.06 | 0.10 | 5.1 | Clear yellow solution free of visible particles |
| CaCl$_2$ | 1:2 | / | / | 8% | absolute ethanol ad 25 mL | START | 0.60 | 0.06 | 0.09 | 3.8 | Clear yellow solution free of visible particles |
| | | | | | | 1 DAY/ 40° C. | 0.70 | 0.07 | 0.09 | 5.0 | Clear yellow solution free of visible particles |
| | | | | | | 7 DAYS/ 2-8° C. | 0.61 | 0.06 | 0.09 | 4.0 | Clear yellow solution free of visible particles |
| | | | | | | 7 DAYS/ 25° C. | 0.65 | 0.06 | 0.09 | 5.3 | Clear yellow solution free of visible particles |
| CaCl$_2$ | 1:1 | DMA 30% (V/V) | / | 8% | absolute ethanol ad 25 mL | START | 0.62 | 0.06 | 0.09 | 3.8 | Clear yellow solution free of visible particles |
| | | | | | | 1 DAY/ 40° C. | 1.3 | 0.08 | 0.11 | 4.8 | Clear yellow solution free of visible particles |
| | | | | | | 7 DAYS/ 2-8° C. | 0.66 | 0.05 | 0.10 | 3.7 | Clear yellow solution free of visible particles |
| | | | | | | 7 DAYS/ 25° C. | 1.3 | 0.06 | 0.11 | 4.8 | Clear yellow solution free of visible particles |
| CaCl$_2$ | 1:2 | DMA 30% (V/V) | / | 8% | absolute ethanol ad 25 mL | START | 0.61 | 0.05 | 0.09 | 3.8 | Clear yellow solution free of visible particles |
| | | | | | | 1 DAY/ 40° C. | 0.83 | 0.07 | 0.11 | 4.3 | Clear yellow solution free of visible particles |
| | | | | | | 7 DAYS/ 2-8° C. | 0.63 | 0.05 | 0.09 | 3.7 | Clear yellow solution free of visible particles |
| | | | | | | 7 DAYS/ 25° C. | 0.83 | 0.06 | 0.10 | 4.3 | Clear yellow solution free of visible particles |
| CaCl$_2$ | 1:1 | / | PEG400 60% (V/V) | 8% | absolute ethanol ad 25 mL | START | 0.63 | 0.06 | 0.10 | 3.9 | Clear yellow solution free of visible particles |
| | | | | | | 1 DAY/ 40° C. | 1.1 | 0.07 | 0.11 | 4.7 | Clear yellow solution free of visible particles |
| | | | | | | 7 DAYS/ 2-8° C. | 0.66 | 0.05 | 0.10 | 3.7 | Clear yellow solution free of visible particles |

TABLE 6-continued

IMPURITY PROFILES OF LIQUID COMPOSITIONS ACCORDING TO EXAMPLE 6 AT DIFFERENT STORAGE CONDITION TEMPERATURE

| Ca$^{2+}$ | Molar ratio DAP:Ca$^{2+}$ | Composition Solvent 1 | Solvent 2 | Water content (w/V) | Solvent 3 | Time point/ Temperature | Anhydro DAP | Beta | Lactone hydrolysis product | Total impurities | Appearance |
|---|---|---|---|---|---|---|---|---|---|---|---|
| | | | | | | 7 DAYS/ 25° C. | 1.1 | 0.06 | 0.11 | 4.7 | Clear yellow solution free of visible particles |
| CaCl$_2$ | 1:2 | / | PEG400 60% (V/V) | 8% | absolute ethanol ad 25 mL | START | 0.62 | 0.06 | 0.09 | 3.9 | Clear yellow solution free of visible particles |
| | | | | | | 1 DAY/ 40° C. | 0.71 | 0.06 | 0.10 | 4.3 | Clear yellow solution free of visible particles |
| | | | | | | 7 DAYS/ 2-8° C. | 0.63 | 0.05 | 0.10 | 3.7 | Clear yellow solution free of visible particles |
| | | | | | | 7 DAYS/ 25° C. | 0.69 | 0.06 | 0.11 | 4.4 | Clear yellow solution free of visible particles |
| CaCl$_2$ | 1:1 | DMA 30% (V/V) | / | 8% | PEG400 ad 25 mL (ca. 56% V/V) | START | 0.63 | 0.07 | 0.10 | 3.9 | Clear yellow solution free of visible particles |
| | | | | | | 1 DAY/ 40° C. | 1.1 | 0.06 | 0.12 | 4.4 | Clear yellow solution free of visible particles |
| | | | | | | 7 DAYS/ 2-8° C. | 0.64 | 0.05 | 0.10 | 3.7 | Clear yellow solution free of visible particles |
| | | | | | | 7 DAYS/ 25° C. | 1.1 | 0.06 | 0.12 | 4.4 | Clear yellow solution free of visible particles |
| CaCl$_2$ | 1:2 | DMA 30% (V/V) | / | 8% | PEG400 ad 25 mL (ca. 56% V/V) | START | 0.58 | 0.05 | 0.09 | 3.7 | Clear yellow solution free of visible particles |
| | | | | | | 1 DAY/ 40° C. | 0.76 | 0.06 | 0.11 | 4.1 | Clear yellow solution free of visible particles |
| | | | | | | 7 DAYS/ 2-8° C. | 0.63 | 0.05 | 0.10 | 3.6 | Clear yellow solution free of visible particles |
| | | | | | | 7 DAYS/ 25° C. | 0.73 | 0.06 | 0.11 | 3.9 | Clear yellow solution free of visible particles |

The invention claimed is:

1. A liquid pharmaceutical formulation comprising daptomycin,
one or more polar protic solvents, and
one or more polar aprotic solvents selected from the group consisting of N-ethylacetamide, N-ethylformamide, N-methyl-N-vinylacetamide, N,N-dimethylpropionamide and N,N-diisopropylformamide.

2. The liquid pharmaceutical formulation according to claim 1, wherein the one or more polar protic solvents are selected from the group consisting of ethanol, benzyl alcohol, 2-methyl-1-propanol, tert butyl alcohol, ethylene glycol, propylene glycol, glycerol, polysorbates, and polyethylene glycol (PEG).

3. The liquid pharmaceutical formulation according to claim 2, where the polysorbates are selected from the group consisting of polysorbate 20, polysorbate 40, and polysorbate 80.

4. The liquid pharmaceutical formulation according to claim 2, wherein one of the one or more polar protic solvents is glycerol.

5. The liquid pharmaceutical formulation according to claim 2, wherein one of the one or more polar protic solvents is polyethylene glycol.

6. The liquid pharmaceutical formulation according to claim 5, where the polyethylene glycol is selected from the group consisting of polyethylene glycol 200 (PEG 200), polyethylene glycol 300 (PEG 300), polyethylene glycol 400 (PEG 400), and polyethylene glycol 600 (PEG 600).

7. The liquid pharmaceutical formulation according to claim 6, wherein the polyethylene glycol is polyethylene glycol 400 (PEG 400).

8. The liquid pharmaceutical formulation of claim 1, further comprising a source of calcium.

9. The liquid pharmaceutical formulation according to claim 8, wherein the source of calcium is calcium chloride (CaCl$_2$)), Ca-α-D-heptagluconate, calcium lactate, or calcium acetate.

10. The liquid pharmaceutical formulation according to claim 9, wherein the molar ratio of daptomycin:calcium is from about 1:1 to about 1:5.

11. The liquid pharmaceutical formulation according to claim 10, wherein the molar ratio of daptomycin:calcium is about 1:1, about 1:2, about 1:3, about 1:4 or about 1:5.

12. The liquid pharmaceutical formulation according to claim 1, further comprising water.

13. The liquid pharmaceutical formulation according to claim 12, wherein the water is present in amount of about 15% (w/V) or less.

14. The liquid pharmaceutical formulation according to claim 1, wherein the concentration of daptomycin is from about 10 mg/mL to about 120 mg/mL.

15. The liquid pharmaceutical formulation according to claim 1, wherein the concentration of the one or more polar protic solvents is from about 30% to about 80% (V/V).

16. The liquid pharmaceutical formulation according to claim 1, wherein the concentration of the one or more polar aprotic solvents is less than 60% (V/V).

17. The liquid pharmaceutical formulation according to claim 1, wherein the concentration of the one or more polar aprotic solvents is from about 5% to about 50%.

18. The liquid pharmaceutical formulation of claim 1, further comprising a solubilizer.

19. The liquid pharmaceutical formulation according to claim 18, wherein the solubilizer is selected from the group consisting of polyoxyl castor oil, polyoxyl 15 hydroxystearate, and soybean oil.

20. A method of treating an infection caused by Gram-positive pathogens comprising administering to the patient a therapeutically effective amount of the liquid pharmaceutical formulation of claim 1 or administering to the patient a therapeutically effective amount of a preparation prepared from the liquid pharmaceutical formulation of claim 1.

21. A process for preparing a liquid pharmaceutical formulation of daptomycin comprising mixing daptomycin, one or more polar protic solvents, and one or more polar aprotic solvents selected from the group consisting of N-ethylacetamide, N-ethylformamide, N-methyl-N-vinylacetamide, N,N-dimethylpropionamide and N,N-diisopropylformamide.

\* \* \* \* \*